United States Patent

Schäfer et al.

[11] Patent Number: 5,552,070
[45] Date of Patent: Sep. 3, 1996

[54] PHOSPHORYLATION OF EPOXIDES

[75] Inventors: Volker Schäfer, Altrip; Robert Kohler, Oberhausen; Günter Schilling, Schwetzingen; Alfred Pauli, Sandhausen; Ingo Röhrs, Rimbach; Joachim Korff, Hockenheim, all of Germany

[73] Assignee: Rhein Chemie Rheinau GmbH, Mannheim, Germany

[21] Appl. No.: 321,580

[22] Filed: Oct. 11, 1994

Related U.S. Application Data

[63] Continuation of Ser. No. 115,642, Sep. 3, 1993, abandoned.

[30] Foreign Application Priority Data

Sep. 17, 1992 [DE] Germany ............ 42 31 073.3

[51] Int. Cl.$^6$ ..................... C10M 137/04
[52] U.S. Cl. ................. 508/224; 554/4; 554/78; 554/79
[58] Field of Search .............. 554/4, 78, 79; 252/32.5, 49.8

[56] References Cited

U.S. PATENT DOCUMENTS 2,490,748 12/1949 Dickey et al.
2,885,363 5/1959 Wolfram et al. .......... 554/78 X
2,965,657 12/1960 Findley .................. 554/79
3,215,715 11/1965 Wurstner.
3,849,321 11/1974 Magne et al. ........... 252/46.7
4,101,432 7/1978 Okorodudu.
4,199,460 4/1980 Sumrell et al. .......... 554/78 X
4,435,338 3/1984 Michaelis et al. ........ 554/78 X

FOREIGN PATENT DOCUMENTS 133030 2/1985 European Pat. Off.
3208748 9/1983 Germany.
388935 6/1965 Switzerland.
8617780 2/1961 United Kingdom.

OTHER PUBLICATIONS

Magne, F. C. et al. *J. Am. Oil Chem. Soc.* 1975, 52(12), 494–497.

Derwent Abstract No. 83–777463; Lottermoser, M., German Patent Application No. DE3208748, published Sep. 1983.

*Primary Examiner*—Johann Richter
*Assistant Examiner*—Michael G. Ambrose
*Attorney, Agent, or Firm*—Connolly & Hutz

[57] ABSTRACT

A process for the phosphorylation of epoxides, in particular of epoxidised fatty acid esters, and the use of the phosphorylation products for the production of lubricants.

1 Claim, No Drawings

PHOSPHORYLATION OF EPOXIDES

This application is a continuation of application Ser. No. 08/115,642 filed on Sep. 3, 1993 now abandoned.

Phosphoric acid and its mono- and diesters react with epoxides to form phosphoric acid hydroxy esters. The following reactions are possible:

According to equation 1, phosphoric acid and its esters 1 react with the epoxide 2 to form a phosphoric acid hydroxy ester derivative 3.

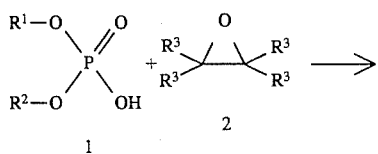

Equation 1

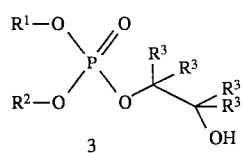

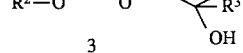

$R^1$ = alkyl, aryl, H       $R^3$ = an organic radical
$R^2$ = alkyl, aryl, H

Scheme 1 describes the addition of phosphoric acid and of its esters to epoxidized fatty acid glycerides. As the reaction scheme shows, the phosphorylation reaction may also give rise to oligomerised triglycerides.

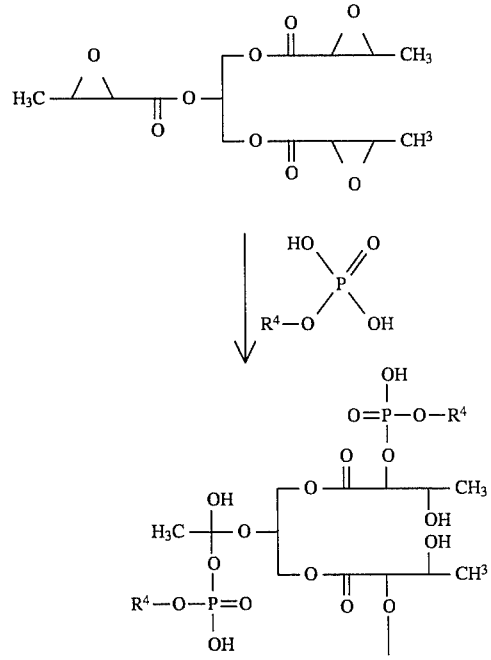

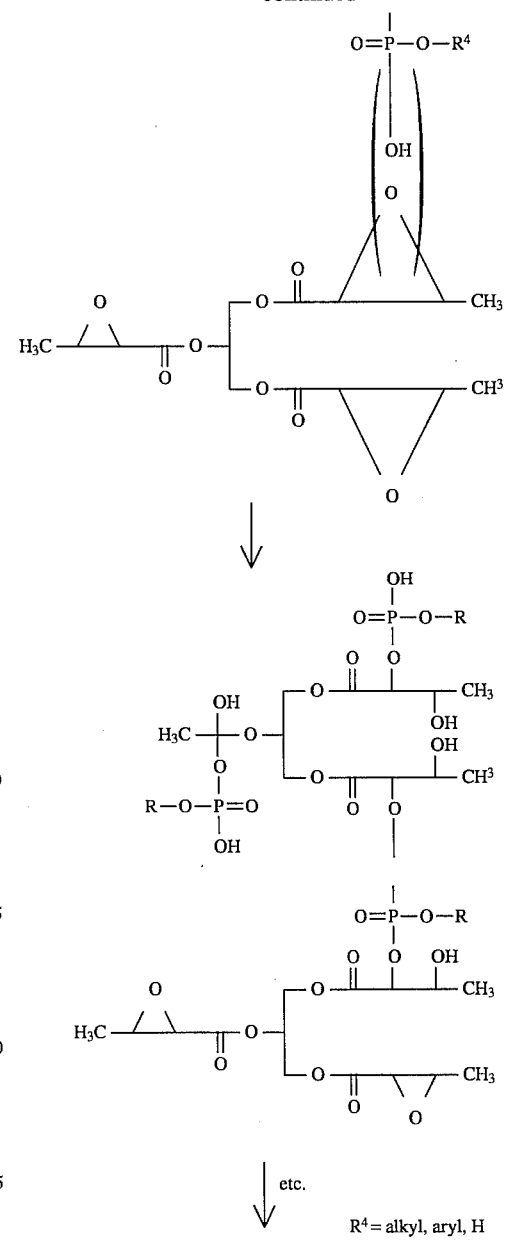

$R^4$ = alkyl, aryl, H

Scheme 1

Tertiary esters of ortho-phosphoric acid with alcohols or phenols are used as plasticizers, fire-resistant hydrolic liquids and compressor oils and oil and fuel additives. They are classified as triaryl, trialkyl or alkylaryl phosphates according to the nature of their alcoholic radicals. The reaction of alcohols with the acid chlorides of phosphoric acid is of technical importance.

It has now been found that the reaction products of phosphoric acid and their mono- and diesters with epoxides, in particular with epoxidized fatty acids and fatty acid derivatives, may be used as lubricant additives.

The invention relates to a process for the phosphorylation of epoxidized fatty acids, e.g. oleic acids, linoleic acids, erucic acids and fatty acid derivatives such as fatty acid esters, e.g. colza oil, soya bean oil or oleic acid methyl ester, characterised in that an epoxidized fatty acid or a derivative thereof having an epoxide content of from 1.5–15% by weight, preferably from 4–8% by weight, is reacted with the phosphoric acid or its ester at 0°–120° C., preferably at 20°–80° C., most preferably at about 40° C. The quantity of phosphoric acid or its ester is calculated to provide about one equivalent of phosphoric acid for each epoxide group.

The invention also relates to the phosphorylated epoxylated fatty acids and fatty acid derivatives obtained as indicated above.

Epoxidized fatty acids and fatty acid derivatives, e.g. fatty acid esters, are in particular epoxidation products of fatty acid glycerides or of their alkyl esters (in particular methyl ester), e.g. of colza oil, soya bean oil, lard oil, etc. having an epoxide content of from 3–10% by weight. They may be used singly or as mixtures. Examples of such mixtures are epoxidized colza oil/epoxidized colza oleic acid methyl ester and epoxidized soya bean oil/epoxidized colza oleic acid methyl ester.

Epoxidized fatty acid esters may also be phosphorylated together with epoxidized hydrocarbons (straight chain or branched) or with epoxidized ether compounds preferably having 6–10 carbon atoms. An example of such compounds is 1-(2-ethyl-hexyloxy)-2,3-epoxypropane/epoxidized soya bean oil.

Phosphoric acid or mono- and diesters of phosphoric acid may be used for phosphorylation. Mono- and dialkylesters having straight chain or branched alkyl groups with a chain length of preferably 4–10 carbon atoms and mono- and diarylesters are particularly suitable.

The phosphorylated fatty acid esters according to the invention act as high pressure additives (EP additives) and wear-resistant additives (AW additives), e.g. in mineral oils, synthetic oils, lubricating fats and naturally occurring oils. Such additives may form iron-phosphorus compounds with the iron from the lubricated machine parts, and these iron-phosphorus compounds substantially reduce the wear on these parts (e.g. roller bearings, gear wheels, tools), thereby increasing their useful life. These compounds also prevent the seizing up of machine parts, especially of rotating machine parts. Further, phosphorylated fatty acid esters also act as corrosion inhibitors and as antioxidants. Better results may also be achieved, for example, in the chip cutting working of metals.

The phosphorylated fatty acid esters may be used e.g. as 0.1 to 1.5% by weight solutions, preferably 0.2 to 1% by weight solutions, in basic oils. With 0.3 to 1% by weight solutions in basic oils it is possible to obtain spherical cup diameters of from 0.3 to 0.4 mm in the four ball tester* or a damaging force stage of 12 in the gear wheel tension testing machine. The four ball apparatus test (VKA) according to ASTM-D-2266 serves to determine characteristic values which should permit high surface pressures in the region of mixed friction between surfaces moving in relation to one another. The testing of lubricants in the FZG gear wheel tension testing machine according to DIN 51354 T.1 is used for determining the maximum stress tolerated by the lubricants (occurrence of furrows and scoring at the flanks of the teeth).
*(test conditions: 1 h /300 N)

BRIEF DESCRIPTION OF THE TEST PROCESS

VKA test DIN 51350 - ASTM D 2783 and D 2266

The lubricant is tested in a four ball tester consisting of a rotating ball (running ball) sliding on three balls (standing balls) identical to the running ball. The testing forces may either be increased stepwise until the four ball tester fails or the diameters of the spherical indentations of the three standing balls may be measured after a predetermined testing time during which a constant testing force is applied.
FZG Test DIN 51354 - ASTM D 1947

Specified gear wheels rotate with the lubricant to be tested at a constant speed and a predetermined initial lubricant temperature. The stress on the flanks of the teeth may be increased stepwise. After termination of the test run or after each force stage in the stepwise test, the changes on the flanks of the teeth (flank damages) are recorded by description, photographs, measurements of roughness or contrast impression.

The weight changes in the test wheels may be determined in addition (gravimetric method).

EXAMPLE 1

AW Additive for mineral oils.

210.5 g of mono/dihexylphosphoric acid ester (molar ratio 1:1) are added to 339 g (1.82 mol) of 1-(2-ethylhexyloxy)-2,3-epoxipropane with stirring at 40° C. within 15 minutes. The reaction is highly exothermic. After a reaction time of 30 minutes, the reaction product obtained may be used as AW additive.

Test results:

| | |
|---|---|
| Appearance: | clear, oily liquid |
| P content: | 5.6% by weight |
| | 0.5% by weight of the additive in refined solvent ISO VG 46 |
| VKA (1500 rpm) (DIN 51 350 T.2) | |
| Product load | 1200 N |
| Scuffing load | 1300 N |
| | 0.4% by weight of the additive in refined solvent ISO VG 46 |
| VKA endurance run (DIN 51 350 T.3) 1 h/300 N | |
| Diameter of indentation | 0.45 mm |
| FZG test, A8.3/90 (DIN 51354) visual damaging force stage | 12 |
| Copper activity (ASTM-D-130) 3 h/100° C. | 1 a Refined solvent ISO VG 46 + 3% by weight additive |
| Humidity chamber Steel quality QQS698 polished with abrasive (DIN 51359) | after 200 h degree of corrosion 0 (no corrosion) Refined solvent ISO VG 46 + 0.8% by weight additive |
| Protection against corrosion in steel (DIN 51585 B) | Degree of corrosion 0 (no corrosion) |

EXAMPLE 2

AW Additive for vegetable oils, polyglycols and synthetic esters 500 g of epoxidized colza oleic acid methyl ester having an epoxide content of 4.9% by weight and 204 g of colza oil are introduced into the reaction vessel with stirring. 150 g of mono-di-2-ethyl hexyl phosphoric acid ester (ratio 1:1) are then added within 5 minutes. The reaction is slightly exothermic. The mixture is left to react for a further 5 minutes. The reaction product obtained may be used without further working up, inter alia as AW additive.

| Test results | |
|---|---|
| Appearance: | pale yellow, highly viscous liquid |
| P content: | 2.34% |
| | 1% by weight additive in synthetic esters |
| VKA endurance run (DIN 51350, T.3) 1 h/300 N Diameter of spherical indentation | 0.3 mm |
| FZG test A8, 3/90 (DIN 51354) visual Damaging force stage | 12 |
| Copper activity (ASTM-D-130) 3 h/100° C. | 1 a |

We claim:

1. A lubricating oil or fat containing 0.1 to 1.5% by weight of a phosphorylated epoxidized fatty acid triglyceride which is produced by reacting an epoxidized fatty acid glyceride with a mixture of mono- and diester of phosphoric acid at 0° to 120° C.

* * * * *